United States Patent [19]

Ferek-Petric et al.

[11] Patent Number: 5,318,595
[45] Date of Patent: Jun. 7, 1994

[54] PACING METHOD AND SYSTEM FOR BLOOD FLOW VELOCITY MEASUREMENT AND REGULATION OF HEART STIMULATING SIGNALS BASED ON BLOOD FLOW VELOCITY

[76] Inventors: Bozidar Ferek-Petric, Sovinec 17; Branko Breyer, Prilaz G. Dezelica 79, both of 41000 Zagreb, Yugoslavia

[21] Appl. No.: 880,552

[22] Filed: May 8, 1992

Related U.S. Application Data

[63] Continuation-in-part of Ser. No. 674,607, Mar. 25, 1991, Pat. No. 5,243,976.

[30] Foreign Application Priority Data

Sep. 25, 1989 [YU] Yugoslavia ............. 1852/89
Sep. 11, 1990 [YU] Yugoslavia ............. 1717/90

[51] Int. Cl.⁵ ............................................. A61N 1/362
[52] U.S. Cl. ............................................. 607/17
[58] Field of Search ........................... 128/419 PG

[56] References Cited

U.S. PATENT DOCUMENTS

| | | | |
|---|---|---|---|
| 3,903,897 | 9/1975 | Woolons et al. | 128/419 PG |
| 3,938,502 | 2/1976 | Bom | 128/2 V |
| 3,942,534 | 3/1976 | Allen et al. | 128/419 PG |
| 4,249,539 | 2/1981 | Vilkomerson et al. | 128/660 |
| 4,291,707 | 9/1981 | Heilman et al. | 128/784 |
| 4,319,580 | 3/1982 | Colley et al. | 128/661 |
| 4,475,551 | 10/1984 | Langer et al. | 128/419 PG |
| 4,535,774 | 8/1985 | Olson | 128/419 PG |
| 4,572,191 | 2/1986 | Mirowski et al. | 128/419 D |
| 4,614,192 | 9/1986 | Imran et al. | 128/419 D |
| 4,662,377 | 5/1987 | Heilman et al. | 128/419 D |
| 4,686,987 | 8/1987 | Salo et al. | 128/419 PG |
| 4,697,595 | 10/1987 | Breyer et al. | 128/660 |
| 4,706,681 | 11/1987 | Breyer et al. | 128/642 |
| 4,766,902 | 8/1988 | Schroeppel | 128/419 PG |
| 4,766,905 | 8/1988 | Namekawa | 128/663 |
| 4,768,911 | 9/1988 | Balter | 414/3 |
| 4,768,912 | 9/1988 | Miura | 414/32 |
| 4,770,177 | 9/1988 | Schroeppel | 128/419 PG |
| 4,771,788 | 9/1988 | Millar | 128/661.09 |
| 4,771,789 | 9/1988 | Namekawa | 128/661.09 |
| 4,773,401 | 9/1988 | Citak et al. | 128/419 PG |
| 4,774,950 | 10/1988 | Cohen | 128/419 D |
| 4,779,617 | 10/1988 | Whigham | 128/419 P |
| 4,790,317 | 12/1988 | Davies | 128/419 D |
| 4,790,322 | 12/1988 | Iinuma | 128/661.10 |
| 4,790,323 | 12/1988 | Leavitt et al. | 128/661.09 |
| 4,791,931 | 12/1988 | Slate | 128/419 PG |
| 4,802,481 | 2/1989 | Schroeppel | 128/419 PG |
| 4,802,490 | 2/1989 | Johnston | 128/661.08 |
| 5,014,698 | 5/1991 | Cohen | 128/419 PG |
| 5,085,215 | 2/1992 | Nappholz et al. | 128/419 PG |
| 5,097,831 | 3/1992 | Lekholm | 128/419 PG |
| 5,139,020 | 8/1992 | Koestner et al. | 128/419 PG |
| 5,156,147 | 10/1992 | Warren et al. | 128/419 PG |
| 5,179,949 | 1/1993 | Chirife | 128/419 PG |

FOREIGN PATENT DOCUMENTS

0311019 4/1989 European Pat. Off. ...... A61N 1/365

*Primary Examiner*—William E. Kamm
*Attorney, Agent, or Firm*—Hill, Steadman & Simpson

[57] ABSTRACT

A system and method for regulation of pacing signals, and more particularly for regulation of an atrioventricular interval in a cardiac electrotherapy system based on measurement of blood flow velocity profiles. More particularly, a diastolic blood flow filling wave and an atrial blood flow filling wave are determined and a time delay between peaks of the two waves and/or a superimposition velocity of the two waves relative to one another are utilized for the regulation. The regulation preferably occurs by comparing the measured time delay to a desired time delay or desired superimposition velocity, and the result of the comparison is then employed for regulating the pacing, or regulating the atrioventricular interval.

12 Claims, 7 Drawing Sheets

DETERMINE DIASTOLIC BLOOD FLOW VELOCITY FILLING E-WAVE AND ATRIAL BLOOD FLOW VELOCITY FILLING A-WAVE, INCLUDING PEAK VELOCITIES THEREOF, IF DESIRED

DETERMINE TIME INTERVAL BETWEEN E AND A-WAVES AND COMPARE TO DESIRED E-A INTERVAL, INCLUDING RATIO BETWEEN TIME INTERVAL AND PACING PERIOD, IF DESIRED

REGULATE PACING SIGNALS AND ATRIAL-VENTRICLE (A-V) INTERVAL BASED ON E-A INTERVAL; AND PROVIDING PACING SYNCHRONOUS WITH FILLING WAVE, AND DECREASING A-V INTERVAL BASED ON PACING RATE, IF DESIRED

FIG. 11

DETERMINE DIASTOLIC BLOOD FLOW VELOCITY FILLING E-WAVE AND ATRIAL BLOOD FLOW VELOCITY FILLING A-WAVE

DETERMINE SUPERIMPOSITION VELOCITY AT WHICH DIASTOLIC FILLING WAVE MEETS ATRIAL FILLING WAVE, AND COMPARE TO DESIRED SUPERIMPOSITION VELOCITY, AND INCLUDING DETERMINING RATIO BETWEEN SUPERIMPOSITION VELOCITY AND PEAK VELOCITY OF DIASTOLIC FILLING WAVE, IF DESIRED

REGULATE PACING SIGNALS AND ATRIAL-VENTRICULAR (A-V) INTERVAL BASED ON MEASURED SUPERIMPOSITION VELOCITY

FIG. 12

```
┌─────────────────────────────────────────────┐
│         DETERMINE DIASTOLIC BLOOD           │
│      FLOW VELOCITY AT TRICUSPID VALVE       │
└─────────────────────────────────────────────┘
                     │
┌─────────────────────────────────────────────────────┐
│ CONTROL PACING SIGNALS BASED ON BLOOD FLOW VELOCITY │
│   AND CONTROLLING AV INTERVAL BASED ON PACING RATE  │
└─────────────────────────────────────────────────────┘
```

FIG. 13

```
┌─────────────────────────────────────────────┐
│      DETERMINE DIASTOLIC BLOOD FLOW VELOCITY│
│             AT TRICUSPID VALVE              │
└─────────────────────────────────────────────┘
                     │
┌─────────────────────────────────────────────────────┐
│ CONTROL PACING SIGNALS BASED ON BLOOD FLOW VELOCITY │
│ AND CONTROLLING VENTRICULAR PACING SYNCHRONOUS WITH │
│   BLOOD FLOW VELOCITY ATRIAL FILLING VALVE TO       │
│         MAINTAIN PHYSIOLOGIC AV INTERVAL            │
└─────────────────────────────────────────────────────┘
```

5,318,595

PACING METHOD AND SYSTEM FOR BLOOD FLOW VELOCITY MEASUREMENT AND REGULATION OF HEART STIMULATING SIGNALS BASED ON BLOOD FLOW VELOCITY

RELATED APPLICATION

The present application is a continuation-in-part of copending application of the same inventors, which has matured into U.S. Pat. No. 5,243,976, issued Sep. 14, 1993, and entitled "TRICUSPID FLOW SYNCHRONIZED CARDIAC ELECTROTHERAPY SYSTEM WITH DOPPLER BLOOD FLOW".

BACKGROUND OF THE INVENTION

This invention relates to cardiac pacing, and more particularly to the optimization of cardiac output in physiologic dual chamber modes of pacing.

Because of the autonomous nervous system regulation of the atrio-ventricular node, the PR interval is usually decreased as the heart rate increases among subjects having a healthy heart. The problem of rate responsive sequential cardiac pacing (DDDR mode) and the P wave synchronous ventricular pacing (VDD mode) is to maintain this natural heart behavior in the case when the heart block prevents the natural atrio-ventricular delay shortening. Therefore, contemporary cardiac pacemakers, especially dual chamber rate responsive models, comprise the "rate responsive AV delay"programming feature. The advantage of such pacemakers is that, due to the reduction in the overall refractory period, the physical capacity of a patient is increased by enabling greater maximum tracking rate. However, the criteria for the software algorhythm which controls this special pacemaker function timing have not been appropriately solved.

Pacemakers currently available on the market and produced by various manufacturers determine the AV delay timing by means of the mathematical relationship between the AV interval and the heart rate. The linear correlation between PR interval and heart rate during exercise was described in the paper "Physiological Relationship Between AV Interval and Heart Rate in Healthy Subjects: Application to Dual Chamber Pacing", published by C. Daubert and co-workers in PACE 9:1032, 1986, incorporated herein. Despite the fact that various manufacturers use various algorhythms including an exponential as well as a linear relationship between heart rate and atrio-ventricular interval shortening, none of them measure some hemodynamic parameter and as a consequence adjust the A-V interval. There is a theoretical possibility in all pacing systems which measure the cardiac output to adjust the A-V interval in order to achieve the maximum cardiac output. In our earlier patent application U.S. Ser. No. 674,607, filed Mar. 25, 1991,and fully incorporated herein, we disclose an electrotherapy system controlled by means of the tricuspid flow waveform. The same system was described in the European patent applications "Cardiac Electrotherapy System" and "Ultrasonic Doppler Synchronized Cardiac Electrotherapy Device" having serial numbers 91104561.5 and 91104555.7, respectively. This system enables the exact optimization of the A-V interval by means of the monitoring of the ventricular filling pattern and keeping the optimal waveform timing. This application is a continuation-in-part of that earlier application.

SUMMARY OF THE INVENTION

It is an object of this invention to enable the physiologic cardiac pacing system to decrease the atrio-ventricular interval as the heart rate increases.

It is a further object of this invention to adjust the atrio-ventricular interval in such a way as to obtain maximum hemodynamic performance.

It is another object of this invention to monitor the ventricular filling waveform pattern and to maintain the optimal filling waveform timing.

It is a further object of this invention to determine a time delay between a diastolic filling wave and an atrial filling wave, and preferably between a peak velocity of the diastolic filling wave and the peak velocity of the atrial filling wave, and to use that time delay for regulating the A-V interval.

According to the invention, the time interval between the diastolic filling wave and the atrial wave, the so-called EA interval, is employed for regulating the atrio-ventricular interval. Preferably the measured EA interval is compared to a desired EA interval, and depending upon the difference between the desired EA interval and the actual EA interval, an atrio-ventricular (A-V) regulation is undertaken.

DESCRIPTION OF THE PREFERRED EMBODIMENTS

Figure 13:
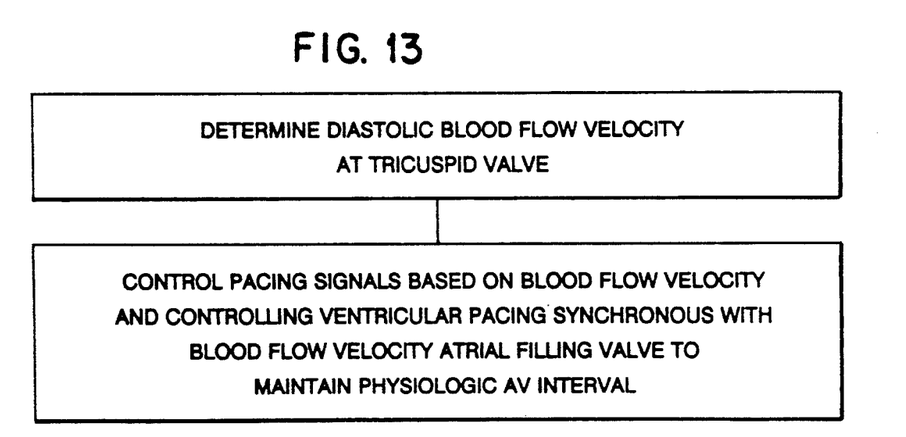

Earlier application Ser. No. 674,607 discloses a flow velocity measurement means for measuring velocity of blood flow in the region of a tricuspid valve between the right auricle and the right ventricle of the heart. Furthermore, pacing means is disclosed for providing pacing signals to the heart. See, for example, FIGS. 1, 5, 6, 7, 8, 9, 10, 11, 15, 16, 17, 18, and 19 showing pacing electrodes and flow velocity measurement transducers, and FIGS. 13 and 14 showing the pacemaker for connection to the pacing electrode and velocity measurement transducer.

Figure 1:
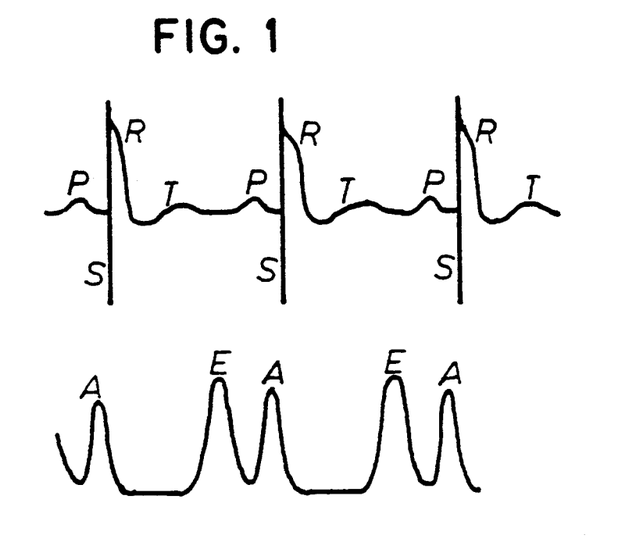
Fig. 1 discloses an electrocardiogram and tricuspid flow waveforms in A-wave synchronous ventricular pacing with a normal A-V interval.

FIG. 1 shows the electrocardiogram of the P-wave synchronous ventricular pacing (VAT mode) with a corresponding tricuspid flow waveform, which is in our invention actually A-wave synchronous ventricular pacing. Every P-wave which is a depolarization of atria is followed by a corresponding A-wave which is a consequence of atrial contraction. After the predetermined A-V delay, the pacing stimulus S occurs and consequently the R-wave, which is the depolarization of the ventricles. A T-wave is a repolarization of ventricles and a corresponding E-wave occurs which is the rapid early diastolic filling as a consequence of ventricular relaxation. In FIG. 1, according to the predetermined atrio-ventricular delay, the E-wave is instantly followed by an A-wave. As the deceleration of the rapid ventricular filling decreases and the velocity declines almost to zero, the atrial filling again accelerates the tricuspid flow up to the peak atrial filling velocity. Therefore, there is a small superimposition of the A-wave on the E-wave. There is a continuous flow through the entire diastolic filling period.

Figure 2:
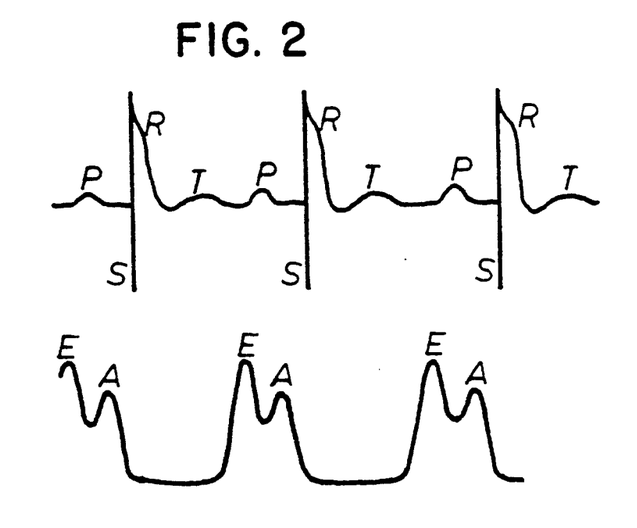
FIG. 2 discloses an electrocardiogram and tricuspid flow waveforms in A-wave synchronous ventricular pacing with a long A-V interval.

FIG. 2 discloses the same waveforms as in the previous figure, having the same atrial rate, but with a longer atrio-ventricular interval. Because the A-V delay is longer, the interval between the pacing spike (and consequent R-wave) and the subsequent P-wave is shorter. Because the QT interval did not change, the interval between the T-wave and the subsequent P-wave is also shorter. As a consequence, the interval between the corresponding E-wave and the corresponding A-wave is shorter. As a repercussion, the superimposition of the A-wave on the E-wave occurs, i.e. the atrial filling acceleration starts at the rapid ventricular filling deceleration portion of the E-wave when flow velocity is still significantly high. The flow velocity at which the atrial filling starts is designated as a superimposition velocity SV. In comparison with the example from the previous figure, the flow is also continuous through the entire diastolic filling period, but the overall integral of the diastolic filling waveform is lower, which means that the quantity of blood transported through the tricuspid valve is slightly decreased. Therefore, also the stroke volume of the subsequent ventricular systole is reduced, in comparison with the example of the previous figure.

Figure 3:
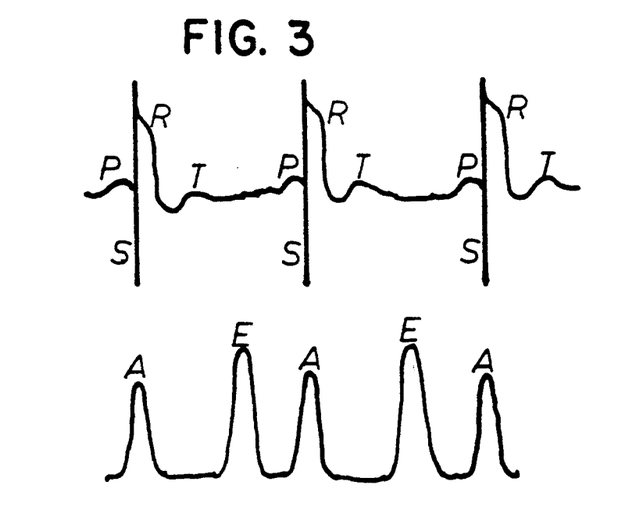
FIG. 3 discloses an electrocardiogram and tricuspid flow waveforms in A-wave synchronous ventricular pacing with a short A-V interval.

FIG. 3 discloses the same waveforms as in previous figures, and having the same atrial rate, but with a nonphysiologic short atrio-ventricular delay. Because the A-V delay is shorter, the interval between the pacing spike (and consequent R-wave) and the subsequent P-wave is longer. Because the QT interval did not change, the interval between the T-wave and the subsequent P-wave is also longer. As a consequence, the interval between the corresponding E-wave and the corresponding A-wave is longer. After the early ventricular filling suspends, the atrial filling starts after a period of zero filling velocity. In the disclosed example, the diastolic filling waveform is discontinuous, contrary to the previous two examples where the waveform is continuously assembled of two components: the E and the A waves. The stroke volume is significantly decreased in this example because of two reasons. Discontinuous flow, i.e. a deceleration of transvalvular flow to zero and the period of zero filling velocity, requires the acceleration of blood from zero velocity by means of the atrial contraction. Therefore, a significant amount of atrial contraction energy is spent for the initial acceleration of the A-wave. Furthermore, the atrial filling is prematurely terminated by ventricular systole which causes the interruption of active atrial blood transport by the subsequent ventricular contraction, causing a less complete diastolic ventricular filling.

Figure 4:
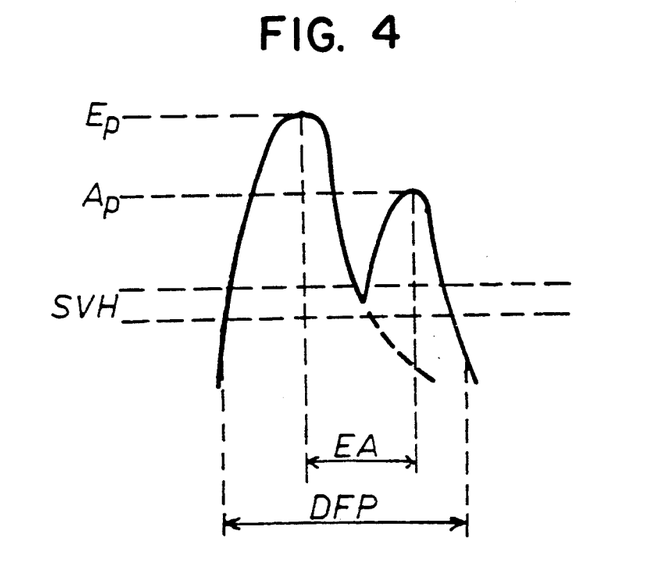
FIG. 4 discloses a tricuspid flow waveform with designation of measurement points.

FIG. 4 is an example of a continuous flow velocity waveform comprising an early filling wave having the peak velocity $E_p$ and the late (atrial) filling wave having the peak velocity $A_p$. There is a mild superimposition of the A-wave on the E-wave. This means that the flow acceleration caused by the atrial contraction begins at a certain flow velocity which we specified as a superimposition velocity. Superimposition velocity is not constant from beat to beat, but, assuming a certain constant atrio-ventricular delay, it is kept within the magnitude interval labelled as a superimposition velocity hysteresis, designated with SVH in the figure. Assuming that the QT interval is constant, the time interval between the E-wave and the A-wave is also constant for the certain constant atrio-ventricular delay and constant heart rate. This time interval is designated on the figure as an EA interval defined as a period of time between two velocity peaks. Another EA interval may be defined as a period of time between the two onsets of the two waves (not shown in the figure), but this one is more sophisticated for measurement in our system.

Superimposition velocity and the EA interval are two parameters which describe the level of superimposition. If the A-V delay is longer, the superimposition is more significant, which means that the superimposition velocity is higher and the EA interval is shorter. If the A-V delay is shorter, the superimposition is less significant, which means that the superimposition velocity is lower and the EA interval is longer.

Figure 5:
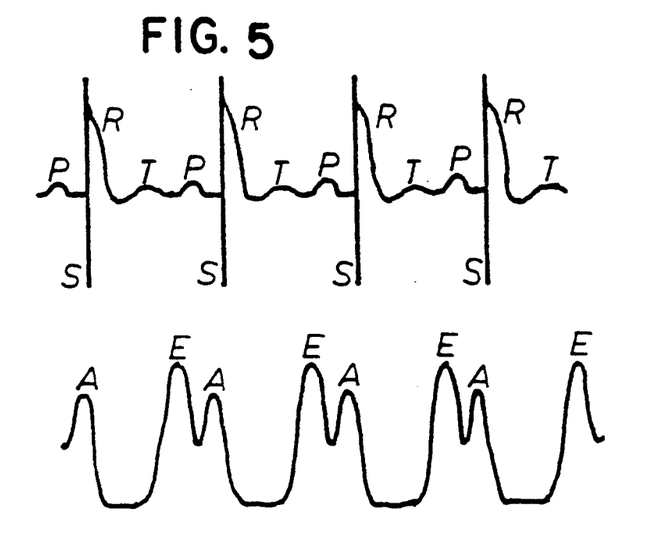
FIG. 5 discloses an electrocardiogram and tricuspid flow waveforms in A-wave synchronous ventricular pacing with a normal A-V interval and atrial tachycardia.

FIG. 5 illustrates how the increase of heart rate inclines the level of superimposition. The A-V delay is the same as in FIG. 1. Because of the autonomous nervous system regulation, the atrial rate increases as well as the QT interval decreases. However, the interval from P-wave to subsequent P-wave, which is the stimulation period in the VAT mode of pacing, decreases more significantly than the QT interval. Therefore, the period between the T-wave and the subsequent P-wave decreases, and consequently the EA interval decreases. Hence, the increase of heart rate increases the level of flow waves superimposition. It is clearly demonstrated in FIG. 5 that the superimposition velocity is higher than in the example of FIG. 1.

Figure 6:
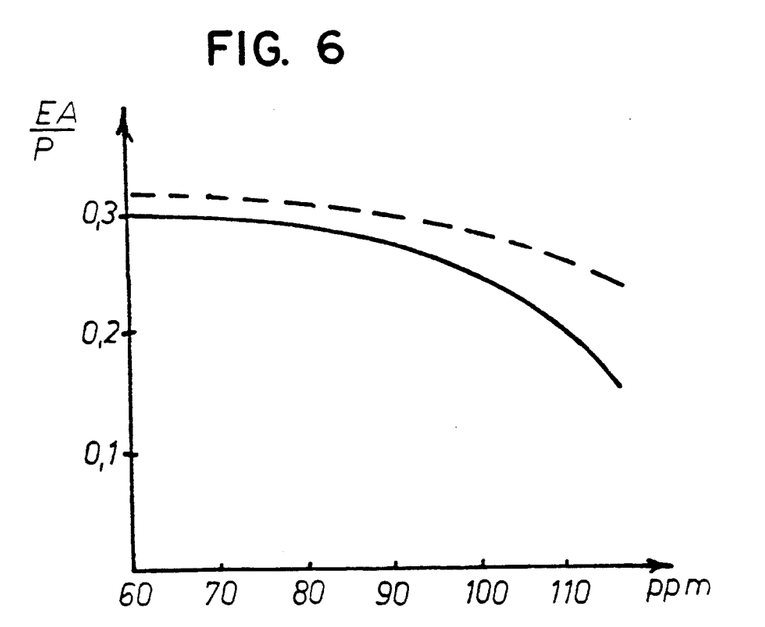
FIG. 6 discloses an EA interval as a function of atrial rate.

FIG. 6 is a diagram showing the EA interval as a function of atrial rate in the VDD mode of pacing (PPM=pulse per minute). The EA interval is shown as a fraction of the pacing period P, which is the inverse of rate. The simple regulation of the atrio-ventricular interval may be achieved by means of the tracking of the EA interval according to a predetermined function stored in the pacemaker microprocessor memory. In order to closely tailor the patient needs, the slope of the function may be programmable, and the dashed line is a function example of a less active patient.

It is understood that the disclosed function is for illustration and is by no means restricted to be different in order to obtain more physiologic A-V delay variation in the individual patient. This means that the atrio-ventricular delay regulation is actually maintaining a certain predetermined level of superimposition which produces the maximum stroke volume. Therefore, the pacemaker must comprise the means for the EA interval measurement as well as the A to A wave interval measurement. According to the measured A to A interval, the corresponding EA interval is read from the memory where the disclosed function is stored. If the measured EA interval is longer than the prescribed EA interval, the A-V delay will be incremented for a predetermined quantity of microprocessor clock pulses. If the EA interval is shorter than the prescribed EA interval, the A-V delay will be decremented for a predetermined quantity of microprocessor clock pulses. The A-V delay is actually the time from the ultrasonic detection of the A-wave and the ventricular pacing stimulus. As is evident from the disclosed examples, this kind of A-V delay is much shorter than the one used in conventional pacemakers where detection of the endocardial P-wave synchronizes the ventricular pacing.

Figure 7:
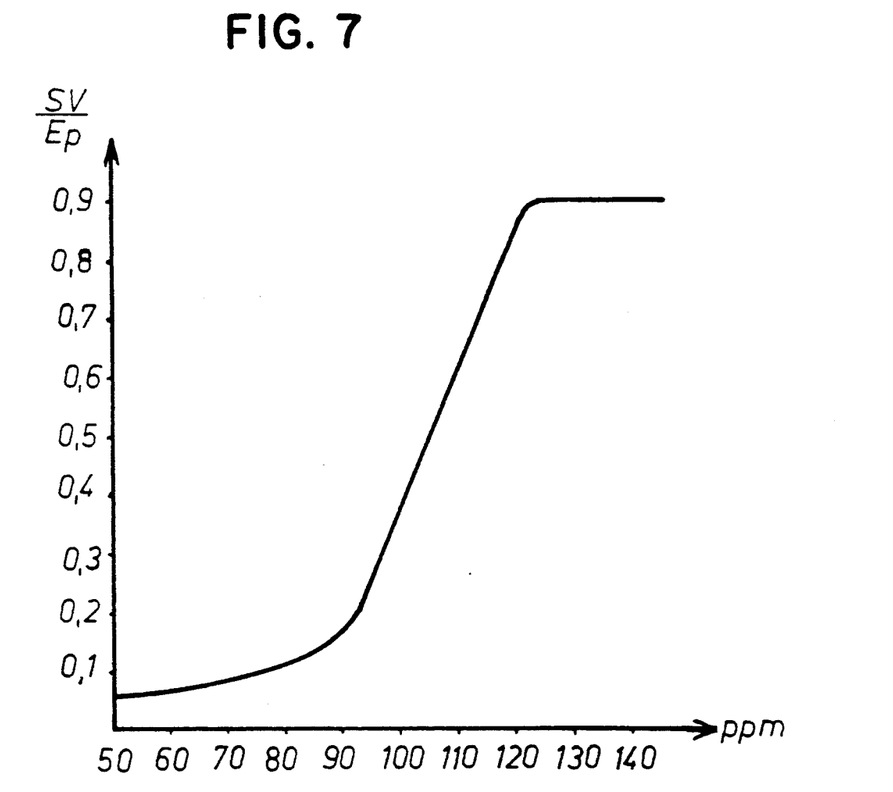
FIG. 7 discloses a superimposition velocity as a function of atrial rate.

FIG. 7 discloses the superimposition velocity SV as a function of the atrial rate. Superimposition velocity is shown as a fraction of peak early filling velocity $E_p$. The important potential of this system is that measurement of peak velocity of the flow wave is possible. The system must also measure the superimposition velocity. Complex and physiologic regulation of the atrio-ventricular interval may be obtained by maintaining the superimposition velocity specified by the disclosed function. The curve consists of three segments. The first one is defined for a low rate range where the superimposition velocity can be kept relatively low, during rest and low physical activity. During mild exercise, the rate increases over 90 ppm, thus elevating the level of superimposition up to the 120 ppm where high superimposition occurs. In the range of high exertion patient exercise, the A-V delay must be kept in order to maintain some level of superimposition which prevents the E-wave and the A-wave from constituting the one superimposed wave, consequently disabling discrimination of the two waves. This is the limitation of the system, and the ability of atrio-ventricular delay regulation to prevent the absolute superimposition in one wave specifies the maximum tracking rate in the individual patient. The disclosed function is only as an example, and individual curves may be found for different patients.

Figure 8:
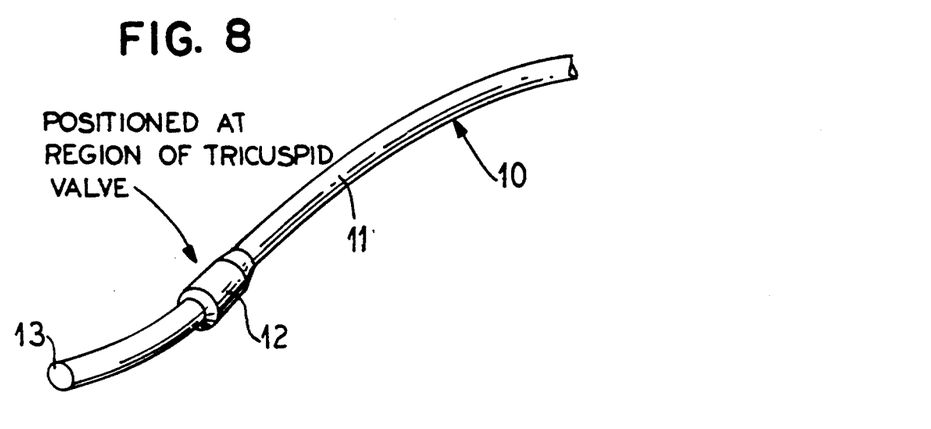
FIG. 8 is a perspective view of a unipolar cardiac pacing lead comprising an axially polarized piezoelectric transducer for pulsed wave flow measurement, with the distal part of the lead being shown.

A pulsed wave flow measurement cardiac pacing lead useful in the present invention is shown in FIG. 8. This pacing lead is described in greater detail in the aforementioned U.S. application, Ser. No. 674,607. In FIG. 8, 10 generally indicates the pacing lead having a plastic body 11, a pacing electrode 13 at the tip, and a pulsed wave flow measurement piezoelectric transducer 12 of cylindrical form built into the lead.

Figure 9:
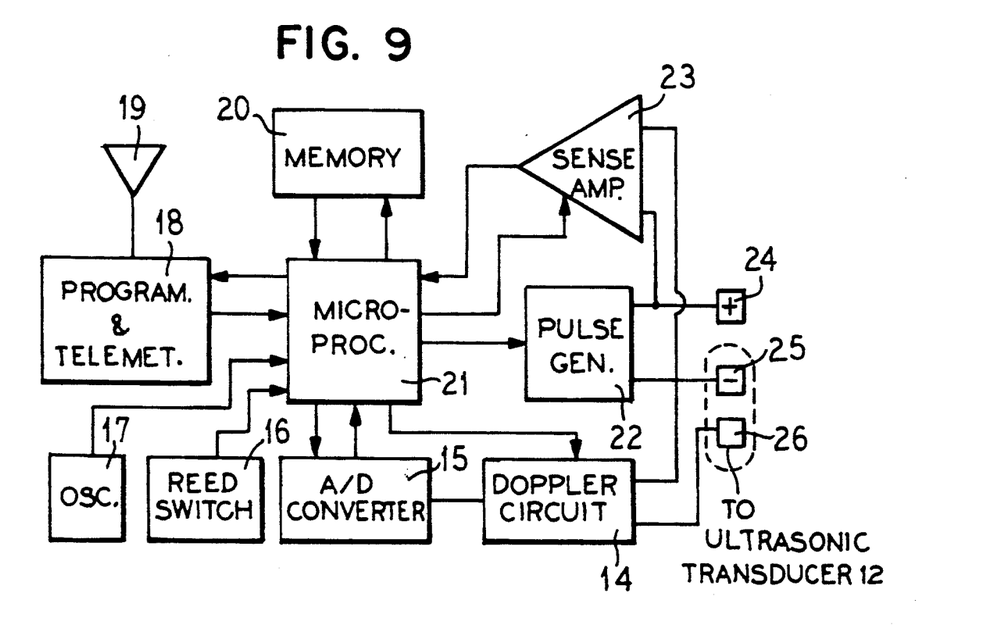
FIG. 9 is a simplified block diagram of a pacemaker comprising a pulse Doppler flow measurement circuit.
Figure 10:
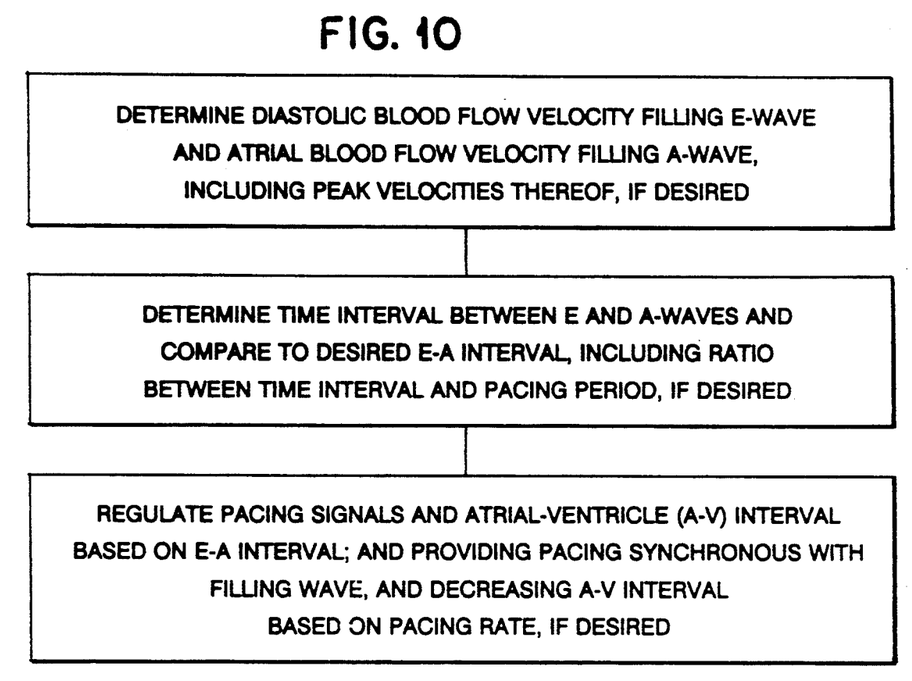
FIGS. 10, 11, 12, and 13 are flow diagrams of various process steps performed by the system of the present invention.
Figure 11:
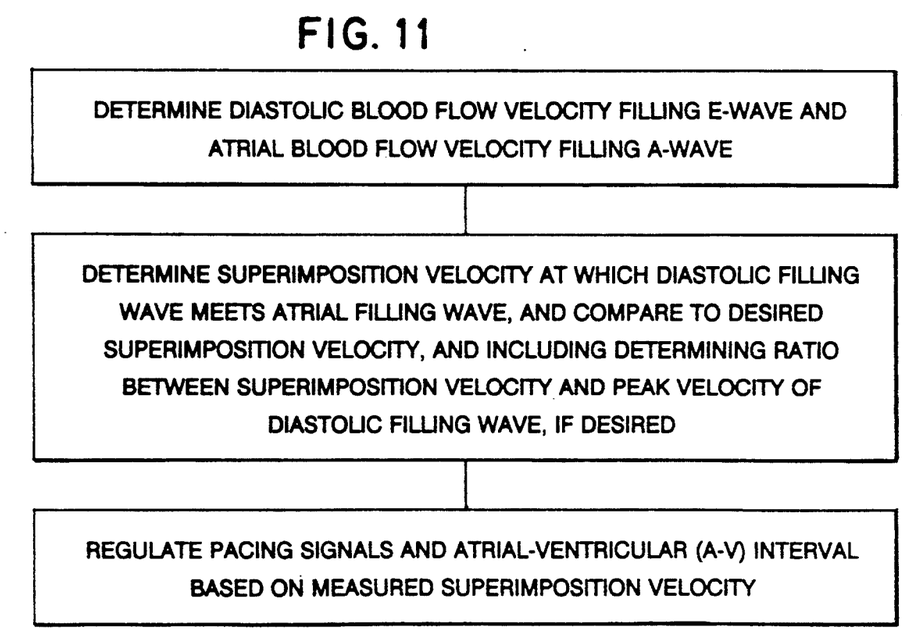
Figure 12:
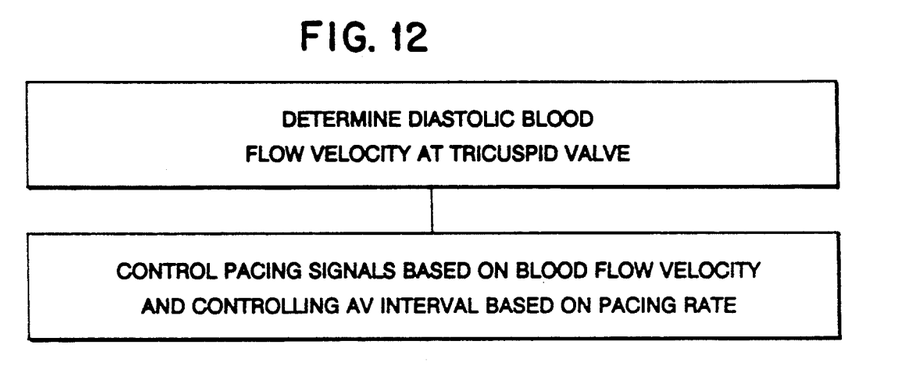

The pacing lead 10 connects to a pacemaker shown in FIG. 9. This pacemaker is described in greater detail in the forementioned U.S. Ser. No. 674,607. Terminal 170 represents the pacemaker can. Terminal 171 is electrically connected to the active pacing electrode 13 in the ventricle as shown in FIG. 8, and also to a lead of the ultrasonic transducer 12 of FIG. 8. Terminal 172 also connects to a lead of the ultrasonic transducer of FIG. 8.

The pacemaker shown in FIG. 9 is formed of a Doppler circuit 14 outputting to an A/D converter 15 connected to a microprocessor 21. The microprocessor drives a pulse generator 22. A reed switch 16 inputs to the microprocessor along the oscillator 17 and program and telemetry 18. 19 is a radio frequency communication circuit with an antenna. A memory 20 also connects to the microprocessor 21 along with an output from sense amplifier 23.

FIGS. 10, 11, 12, and 13 are flow diagrams for the method steps of the invention performed by the pacemaker shown in FIG. 9 and connecting to the cardiac pacing wave containing ultrasonic transducer 12 shown in FIG. 8

Although various minor changes and modifications might be proposed by those skilled in the art, it will be understood that we wish to include within the claims of the patent warranted hereon all such changes and modifications as reasonable come within our contribution to the art.

We claim as our invention:

1. A system for regulating an atrio-ventricular (A-V) interval in a cardiac electrotherapy system, comprising:
   flow velocity measurement means for measuring blood flow velocity at a region of a valve between an atrial chamber and a ventricular chamber to determine a diastolic blood flow velocity filling wave (E wave) and an atrial blood flow velocity filling wave (A wave);
   means for determining a time interval (EA interval) between the diastolic blood flow filling wave and the atrial blood flow filling wave; and
   means for regulating the atrio-ventricular (A-V) interval based on the measured EA interval.

2. A system according to claim 1 including means for comparing the measured EA interval to a desired EA interval, and based on the comparison, for regulating the A-V interval.

3. A system according to claim 1 including means for measuring a superimposition velocity where the E filling wave joins the A filling wave and for utilizing the measured superimposition velocity for regulation of the A-V interval.

4. A system for regulating an atrio-ventricular (A-V) interval in a cardiac electrotherapy system, comprising:
   flow velocity measurement means for measuring blood flow velocity at a region of a valve between an atrial chamber and a ventricular chamber for determining a diastolic blood flow velocity filling wave (E wave) and an atrial blood flow velocity filling wave (A wave);
   means for determining a time interval (EA interval) between the diastolic blood flow filling wave and the atrial blood flow filling wave;
   means for generating pacing signals to the heart; and
   means for employing the EA interval when regulating the pacing signals to the heart.

5. A method for regulating an atrio-ventricular (A-V) interval in a cardiac electrotherapy system, comprising the steps of:
   determining a diastolic blood flow velocity filling wave (E wave) and an atrial blood flow velocity filling wave (A wave) at a region of a valve between an atrial chamber and a ventricular chamber;
   determining a time interval (EA interval) between the diastolic blood flow filling wave and the atrial blood flow filling wave; and
   regulating the atrio-ventricular (A-V) interval based on the measured EA interval for cardiac electrotherapy.

6. A method for regulating an atrio-ventricular (A-V) interval in a cardiac electrotherapy system, comprising the steps of:
   determining a diastolic blood flow velocity filling wave (E wave) and an atrial blood flow velocity filling wave (A wave) at a region of a valve between an atrial chamber and a ventricular chamber;

determining a time interval (EA interval) between the diastolic blood flow filling wave and the atrial blood flow filling wave;

generating pacing signals to the heart; and employing the EA interval to regulate the pacing signals to the heart.

7. A cardiac electrotherapy system, comprising:

flow velocity measurement means for determining a diastolic blood flow velocity filling wave (E-wave) and an atrial blood flow velocity filling wave (A-wave) at a region of a valve between an atrial chamber and a ventricular chamber;

means for determining a parameter indicating a relationship between the diastolic blood flow filling wave and the atrial blood flow filling wave;

means for generating stimulating signals to the heart; and means for regulating the stimulating signals to the heart based on said parameter.

8. A system according to claim 7 wherein said parameter comprises a time interval between the diastolic blood flow filling wave and the atrial blood flow filling wave.

9. A system according to claim 7 wherein said parameter comprises a superimposition velocity at which the diastolic filling wave meets the atrial filling wave.

10. A method for cardiac electrotherapy comprising the steps of:

determining a diastolic blood flow velocity filling wave (E-wave) and an atrial blood flow velocity filling wave (A-wave) at a region of a valve between an atrial chamber and a ventricular chamber;

determining a parameter indicating a relationship between the diastolic blood flow filling wave and the atrial blood flow filling wave;

generating stimulating signals to the heart; and regulating stimulating signals to the heart based on said parameter.

11. A method according to claim 10 wherein said parameter comprises a time interval between the diastolic blood flow filling wave and the atrial blood flow filling wave.

12. A method according to claim 10 wherein said parameter comprises a superimposition velocity at which the diastolic filling wave meets the atrial filling wave.

* * * * *